US009877992B2

(12) United States Patent
Cheng

(10) Patent No.: US 9,877,992 B2
(45) **Date of Patent: *Jan. 30, 2018**

(54) WATER EXTRACTS OF CINNAMON AND RADIX ASTRAGALI

(71) Applicant: Nanzheng Cheng, Foster City, CA (US)

(72) Inventor: Nanzheng Cheng, Foster City, CA (US)

(73) Assignee: Nanzheng Cheng, Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/416,945

(22) Filed: Jan. 26, 2017

(65) Prior Publication Data

US 2017/0136082 A1 May 18, 2017

Related U.S. Application Data

(63) Continuation-in-part of application No. PCT/US2015/042215, filed on Jul. 27, 2015, which is a continuation-in-part of application No. 14/444,873, filed on Jul. 28, 2014, now Pat. No. 9,089,577.

(51) Int. Cl.

*A61K 36/54* (2006.01)
*A61K 36/24* (2006.01)
*A61K 36/00* (2006.01)
*A61K 36/481* (2006.01)

(52) U.S. Cl.

CPC ............ *A61K 36/54* (2013.01); *A61K 36/481* (2013.01)

(58) Field of Classification Search

None

See application file for complete search history.

(56) References Cited

U.S. PATENT DOCUMENTS

| | | | |
|---|---|---|---|
| 6,200,569 | B1 | 3/2001 | Cheng |
| 2008/0102137 | A1 | 5/2008 | Guffy |

FOREIGN PATENT DOCUMENTS

| | | | |
|---|---|---|---|
| CN | 101485825 | A | 7/2009 |
| CN | 102319341 | B | 1/2012 |
| CN | 101336974 | B | 5/2012 |
| CN | 102847063 | A | 1/2013 |

OTHER PUBLICATIONS

Crawford; "Effectiveness of Cinnamon for Lowering Hemoglobin A1C in Patients with Type 2 Diabetes: A Randomized, Controlled Trial"; J. Am. Board Fam. Med; vol. 22, No. 5, pp. 507-512 (2009).

Khan, et al.; "Cinnamon Improves Glucose and Lipids of People With Type 2 Diabetes"; Diabetes Care; vol. 26, No. 12, pp. 3215-3218 (Dec. 2003).

Kim, et al.; "Relative contributions of insulin resistance and β-cell dysfunction to the development of Type 2 diabetes in Koreans"; Diebet. Med.; vol. 30, No. 9, pp. 1075-1079 (Sep. 2013). [English Abstract only].

Lee, et al.; "Nutritional Supplements and Their Effect on Glucose Control"; Curr. Diab. Rep.; vol. 11, pp. 142-148 (2011).

Mang, et al.; "Effects of a cinnamon extract on plasma glucose, $HbA_{1c}$, and serum lipids in diabetes mellitus type 2"; European Journal of Clinical Investigation; vol. 36, pp. 340-344 (2006).

Miura, et al; "Hyopglycemic Activity of the Fruit of the Momordica charantia in Type 2 Diabetic Mice"; J. Nutr. Sci. Vitaminol; vol. 47, pp. 340-344 (2001).

Soloman, et al.; "Effects of short-term cinnamon ingestion on in vivo glucose tolerance"; Diabetes, Obesity and Metabolism; vol. 9, pp. 895-901 (2007).

Song, et al.; "Insulin sensitivity and insulin secretion determined by homeostasis model assessment and risk of diabetes in a multiethnic cohort of women: the Women's Health Initiative Observational Study"; Diabetes Care; vol. 30, No. 7, pp. 1747-1752 (Jul. 2007). [English Abstract only].

Wang, et al.; "Effects of extract of Begonia fimbristipula on the development of diabetic nephrophathy rats"; Chinese J. Biochemical Pharmaceutics; vol. 33, pp. 272-277 (2012). [with English Abstract].

Xie, et al.; "Diabetes is an inflammatory disease: evidence from traditional Chinese medicines"; Diabetes, Obesity and Metabolism; vol. 13, pp. 289-301 (2011).

Cao, et al., "Cinnamon extract regulates glucose transporter and insulin-signaling gene expression in mouse adipocytes", (2010) Phytomedicine 17: 1027-1032.

Mertz, W., "Chromium in Human Nutrition: A Review", (1993) J. Nutr. 123:626-633.

Liu, et al., Astragalus polysaccharide improves insulin sensitivity in KKAy mice: Regulation of PKB/GLUT4 signaling in skeletal muscle, (2010) J. Ethnopharmacology 127:32-37.

Mao, et al., "Astragalus polysaccharide reduces hepatic endoplasmic reticulum stress and restores glucose homeostasis in a diabetic KKAy mouse model", (2007) Acta Pharmacol Sin. 28 (12): 1947-1956.

International Search Report dated Jan. 21, 2016 of PCT/US2015/042215 (2 pages).

*Primary Examiner* — Chris R Tate
*Assistant Examiner* — Russell Fiebig
(74) *Attorney, Agent, or Firm* — Perkins Coie LLP; Viola T. Kung

(57) ABSTRACT

This invention relates to methods and compositions for providing improved insulin-sensitivity and/or enhanced insulin-like action, which leads to improved glucose uptake and utilization. This invention also relates to methods and compositions for lowering LDL, lowering triglycerides, increasing HDL, and lowering high blood pressure in a subject. The methods comprise administering to a subject an effective amount of a water extract of cinnamon and an effective amount of a water extract of *Radix Astragali*.

8 Claims, 1 Drawing Sheet

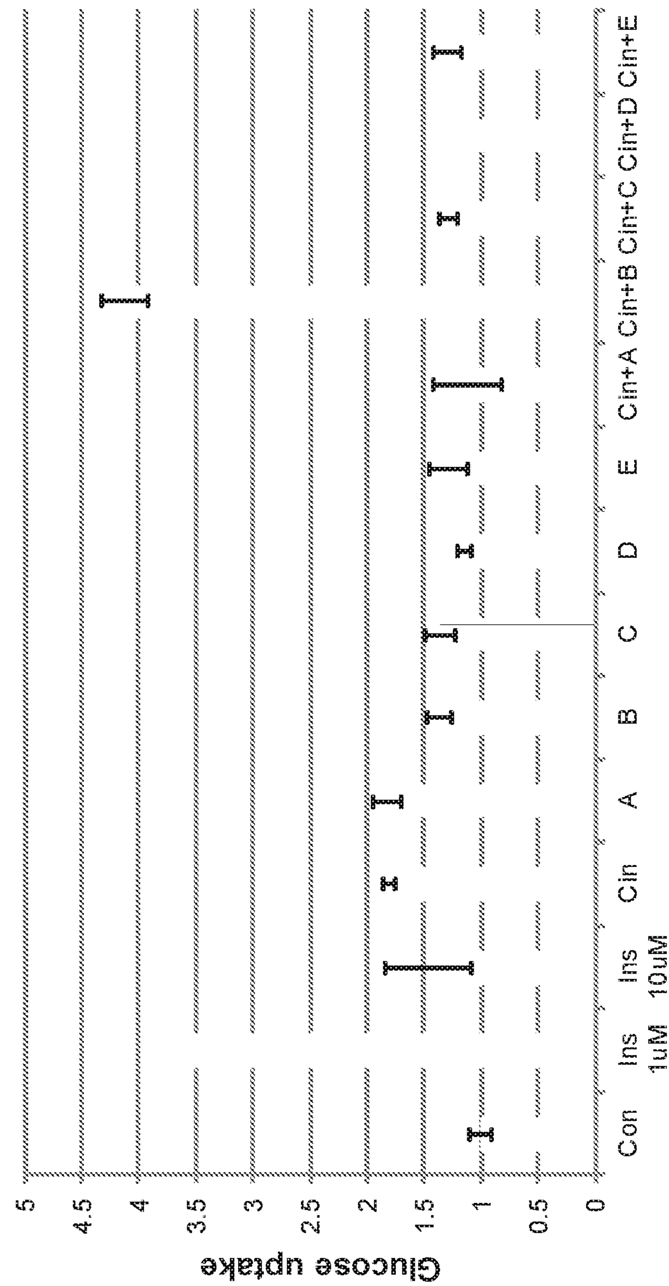
Glucose uptake
0
0.5
1
1.5
2
2.5
3
3.5
4
4.5
5
Con
Ins 1uM
Ins 10uM
Cin
A
B
C
D
E
Cin+A
Cin+B
Cin+C
Cin+D
Cin+E

WATER EXTRACTS OF CINNAMON AND RADIX ASTRAGALI

This application is a continuation-in-part of PCT/US2015/042215, filed Jul. 27, 2015; which claims the priority of U.S. application Ser. No. 14/444,873, filed Jul. 28, 2014, now U.S. Pat. No. 9,089,577. The contents of the above-identified applications are incorporated herein by reference in their entireties.

TECHNICAL FIELD

This invention relates to a composition comprising a water extract of cinnamon and a water extract of *Radix Astragali*. The composition enhances insulin sensitivity and/or provides an insulin-like action.

BACKGROUND OF THE INVENTION

Diabetes mellitus is a major public health problem. In the United States, there are over 10 million patients with diabetes. Diabetes is a syndrome that is caused by a relative or an absolute lack of insulin. Clinically, it is characterized by symptomatic glucose intolerance as well as alterations in lipid and protein metabolism. The maintenance of normal blood sugar levels is achieved by the actions of several hormones, most notably insulin, but also glucagon, epinephrine, corticosteroids, and growth hormone. On the other hand, hyperglycemia is exemplified by higher than normal concentrations of glucose in the blood. The pancreas produces insulin which is released in response to increased blood glucose concentrations. Insulin works to lower the blood sugar levels by stimulating the uptake of glucose by cells. Glucose is used in cellular metabolism to produce energy, or is converted to glycogen for storage in the liver and muscles, or is used in the production of triglycerides and fats.

Crawford (*J Am Board Fam Med,* 22: 507-512, 2009) reports the effectiveness of cinnamon for lowering hemoglobin A1C in patients with type 2 diabetes.

Khan et al (*Diabetes Care,* 26: 3215-3218, 2003) report that intake of 1, 3, or 6 g of cinnamon per day reduces serum glucose, triglyceride, LDL cholesterol, and total cholesterol in people with type 2 diabetes.

Solomon et al (*Diabetes Obes Metab,* 9:895-901, 2007) report that cinnamon ingestion reduced total plasma glucose responses to oral glucose ingestion, as well as improving insulin sensitivity as assessed by insulin sensitivity index.

Water extracts of cinnamon exhibit an insulin potentiating activity, i.e. they increase apparent insulin activity as measured by increased glucose uptake by cells (U.S. Pat. No. 6,200,569).

Mang et al (*European J. Clin. Invest.* 36:340-344, 2006) report that diabetes mellitus type 2 patients treated with 3 g of cinnamon water extract powder per day for 4 months decreased fasting plasma glucose level, in comparison with placebo-treated patients.

Traditional Chinese medicines such as *Radix Astragali, Radix Rehmanniae*, and *Rhizoma Coptidis* can lower blood glucose and control inflammation (Xie et al, *Diabetes Obes Metab,* 2011, 13:289-301). The water extract of the fruit of *Momordica charantia* L. was reported to reduce the blood glucose of KK-AY mice 3 weeks after oral administration (Miura et al., *J. Nutr. Sci. Vitaminol,* 2001, 47: 340-344). The exact of *Begonia fimbristipula* was reported to improve kidney filtration function and improve the clinical symptoms of diabetic nephropathy rats (Wang et al., *Chinese J. Biochemical Pharmaceutics,* 2012, 33: 272-277).

Kim et al (*Diabet Med.,* 30:1075-9, 2013) analyzed the clinical and laboratory data of over 17,000 Korean adults who underwent routine medical examinations with a median interval of 3.5 years to study relative contributions of insulin resistance and β-cell dysfunction to the development of type 2 diabetes in over 17,000 Koreans. Kim et al report that among the participants who developed diabetes, 29% demonstrated predominant β-cell dysfunction dysfunction and 51% had predominant insulin resistance.

Song et al (*Diabetes care,* 30:1747-52, 2007) report that high homeostasis model assessment (HOMA) of insulin resistance and low HOMA of β-cell function were independently and consistently associated with an increased diabetes risk in a multiethnic cohort of U.S. postmenopausal women.

SUMMARY OF THE INVENTION

The present invention is directed to a method for increasing glucose uptake in a subject. The method comprises administering to a subject an effective amount of a water extract of cinnamon and an effective amount of a water extract of *Radix Astragali.*

The present invention is also directed to a method for regulating blood glucose level in a subject. The method comprises administering to a subject an effective amount of a water extract of cinnamon and an effective amount of a water extract of *Radix Astragali.*

The present invention is also directed to a method for decreasing blood glucose level in a hyperglycemic subject. The method comprises administering to a hyperglycemic subject an effective amount of a water extract of cinnamon and an effective amount of a water extract of *Radix Astragali.*

The present invention is also directed to a method of lowering low density lipoprotein (LDL)-cholesterol and/or triglycerides in the blood of a subject. The method comprises administering to a subject in need thereof an effective amount of a water extract of Cinnamon bark and an effective amount of a water extract of *Radix Astragali.*

The present invention is also directed to a method of increasing high density lipoprotein (HDL)-cholesterol in the blood of a subject. The method comprises administering to a subject in need thereof an effective amount of a water extract of Cinnamon bark and an effective amount of a water extract of *Radix Astragali.*

The present invention is further directed to a method of decreasing high blood pressure in subject. The method comprises administering to a subject in need thereof an effective amount of a water extract of Cinnamon bark and an effective amount of a water extract of *Radix Astragali.*

BRIEF DESCRIPTION OF THE DRAWINGS

FIG. 1 shows glucose uptake results of different test compounds relative to control (normalized to 1), by measuring the fluorescent intensity produced by cells. Con=control, Ins=insulin, Cin=water extract of cinnamon, A=water extract of roots of *Rhizoma Coptdis*, B=water extract of roots of *Radix Astragali*, C=water extract of roots of Chinese Foxglove, D=water extract of dried melon of *Momordica Charantiap*, and E=water extract of dried leaves of *Begonia Fimbristipulata Hance.*

DETAILED DESCRIPTION OF THE INVENTION

The effect of insulin to acutely stimulate glucose uptake into muscle and adipose tissue is essential for normal glucose homeostasis. Glucose transport is the rate-limiting step for glucose utilization in muscle at most physiologic glucose and insulin levels, as well as in type 2 and type 1 diabetes. Progressive defects in insulin sensitivity and insulin secretion contribute to the development of diabetes.

This invention relates to methods and compositions for providing improved insulin-sensitivity and/or enhanced insulin-like action, which leads to improved glucose uptake and utilization. Increased insulin sensitivity (i.e., decreased insulin resistance) leads to decreasing blood glucose levels in hyperglycemic patients. Increased insulin sensitivity lowers the risk to the development to type 2 diabetes in a normal subject or a pre-diabetes subject. Increased insulin sensitivity also leads to lowering total cholesterol, lowering LDL-cholesterol, lowering triglycerides, and decreasing high blood pressure, which are associated with decreased risk of type 2 diabetes and cardiovascular diseases. Increased insulin sensitivity also leads to increasing HDL-cholesterol.

Cinnamon or water extracts of cinnamon have been shown to be beneficial in subjects with varying degrees of glucose intolerance ranging from normal to type 2 diabetes.

The inventor intended to select and identify a Chinese traditional medicine that when combined with water extract of cinnamon, the overall insulin sensitivity and/or insulin-like activity are significantly enhanced, and the efficacy of the combined water extracts for regulating blood glucose and/or treating diabetes is boosted.

The inventor discovered that several Chinese traditional medicines, when combined with cinnamon, did not increase the insulin sensitivity and/or enhance insulin-like activity of cinnamon, even the Chinese traditional medicine by itself was reported to have some effect in lowering blood glucose level. For example, when the water extract of cinnamon was combined with a water extract of roots of *rhizoma coptdis*, roots of Chinese foxglove (also known as *Radix Rehmanniae*), dried melon of *Momordica Charantiap*, or dried leaves of *Begonia Fimbristipulata Hance*, the insulin sensitivity or insulin-like activity of cinnamon was not increased at all by the addition of another herb.

The inventor has discovered that combined administration of a water extract of cinnamon and a water extract of *Radix Astragali* provides an enhanced insulin sensitivity and/or insulin-like action. The inventor has discovered that combined administration of a water extract of cinnamon and a water extract of *Radix Astragali* provides a better activity of increasing glucose uptake than each water extract alone. In one embodiment, combined administration of a water extract of cinnamon and a water extract of *Radix Astragali* provides at least an additive activity. In a preferred embodiment, combined administration of a water extract of cinnamon and a water extract of *Radix Astragali* provides a synergistic activity.

The insulin sensitivity or insulin-like activity, for example, can be determined by increased glucose uptake by adipocytes (fat cells). Glucose uptake can be determined by measuring the amount of fluorescent labelled glucose taken up in the cells.

The present invention is directed to a method for increasing insulin sensitivity in a subject. By increasing insulin sensitivity, the present invention provides a method for increasing glucose uptake in a subject. The present invention also provides a method for regulating blood glucose level in a subject.

By increasing insulin sensitivity, the present invention provides a method of decreasing blood glucose level and/or glycosylated hemoglobin level in a hyperglycemic subject. The present invention also provides a method for preventing a normal subject or a pre-diabetic subject from developing type 2 diabetes. The present invention provides a method of lowering triglycerides, lowering total cholesterol, lowering LDL-cholesterol, increasing HDL-cholesterol, and decreasing high blood pressure in a subject such as Type 2 diabetic subject.

In one embodiment, the method comprises administering to a subject an effective amount of a water extract of cinnamon and an effective amount of a water extract of *Radix Astragali*, wherein said water extracts are administered in an amount effective to increase insulin sensitivity or cause an insulin-like action in the subject. "An effective amount," as used herein, refers to an amount that is effective to increase insulin sensitivity or provide an insulin-like action in a subject. In one embodiment, this method does not contain a step of administering to a subject an additional active ingredient (other than cinnamon or *Radix Astragali*) that provides insulin-like action. The two water extracts cinnamon and *Radix Astragali* can be administered simultaneously in one composition or in two separate compositions. Alternatively, the two water extracts can be administered sequentially.

In another embodiment, the method comprises administering to a subject a composition consisting essentially of an effective amount of a water extract of Cinnamon and an effective amount of a water extract of *Radix Astragali*, wherein said water extracts are administered in an amount effective to cause an insulin-like action and to increase glucose uptake in the subject. "Consisting essentially of" refers that the active ingredients of the composition only contain cinnamon and *Radix Astragali*, and do not contain any other active ingredient that increases insulin sensitivity or provides insulin-like action.

The weight ratio of the water extract of cinnamon and the water extract of *Radix Astragali* used in the present methods is in general from about 5:1 to 1:5, 3:1 to 1:3, or 2:1 to 1:2; with about 1:1 to 1:2 or about 1:1 to 1:3 being preferred. About equal weight ratio (1:1) of cinnamon to *Radix Astragali* is more preferred. "About" as used herein, refers to ±10% of the recited value.

The present invention is useful in treating mammalian subjects, such as humans, dogs and cats. The present invention is particularly useful in treating humans. The subject can be a normal subject, a pre-diabetic subject, or a subject suffering from a disease or a disorder, such as a hyperglycemia subject or a type 2 diabetic subject.

Preferred source of a raw material of cinnamon is bark from a cinnamon tree, in the family of *Cinnamomum*. Preferred species are *Cinnamomum mairei, Cinnamomum zeylanicum, Cinnamomum burmannii*, and *Cinnamomum cassia. Cinnamomum mairei* is a tree with highly aromatic bark; its bark can be used for preparing extracts. Commercial *Cinnamomum* bark, which is the dried inner bark of the shoots, and ground cinnamon obtained from a grocery store can also be used for preparing extracts.

*Radix Astragali* is the dried root of perennial herbs, *Astragalus membranaceus* (Fisch.) Bunge and *Astragalus mongholicus* Bunge (Fabaceae). *Radix Astragali* is also named *Astragalus* root, *Astragalus propinquus*, huang-chi, huangqi, hwanggi, membranous milkvetch, milkvetch, Mongolian milk-vetch, neimeng huangqi, ogi, ougi, zhongfengnaomaitong. Major chemical constituents in *Radix Astragali* are triterpene saponins (astragalosides I-X and isoastragalosides I-IV), and polysaccharides (e.g. astragalan, astraglucan AMem-P)

Cinnamon and *Radix Astragali* used in this invention are natural substances derived from herbs, and are safe for human consumption.

Water extracts of Cinnamon and *Radix Astragali* can be prepared according to the procedures described in U.S. Pat. No. 6,200,569, which is incorporated herein by reference in its entirety. In brief, the source tissue is obtained either as a ground powder or is prepared by cutting the plant tissue into small pieces, pulverizing it, grinding it or otherwise increasing the surface area of the pieces of tissue to facilitate extraction. Hydrophilic solvents such as water are used for extraction. Because it is safe, easy to use, and economic, water is a preferred solvent for extraction. A small amount of buffer can be added to water to maintain the pH. A small amount of ethanol or methanol also can be added to water as a solvent for extraction. The amount of solvent added to the raw material for extraction is, in general, in a volume ranging from 2-200 times per unit weight of the raw material, and preferably 20-100 times per unit weight.

Other solvents which can be used include dilute acids and bases. Dilute acids, such as acetic acid and hydrochloric acid also can be used: the acid concentration should be less than about 1 N, and preferably less than 0.5 N. For example, 0.1 N acetic acid or 0.1 N hydrochloric acid can be an effective solvent. Dilute bases, for example, ammonium hydroxide or sodium hydroxide, can be used as a solvent; the concentration of the base should be less than about 1 N and preferably less than 0.5 N. For example, 0.1 N $NH_4OH$ can be used as an effective solvent to extract insulin potentiating activity.

The extraction can be performed at a wide range of temperatures, but preferably at a temperature range from room temperature to about 100° C., for from about 15 minutes to overnight.

After extraction, the liquid which contains the insulin-like activity is separated from any solid debris by centrifugation or filtration. If acid or base is used as the solvent for extraction, the extract usually is neutralized before further usage.

The water extract, which is free of solid debris, can be used directly, or the water extract can be lyophilized or dried to form a powder. The liquid or the powder can be incorporated into a variety of basic materials in the form of a liquid, powder, tablets, or capsules to provide an insulin-like activity.

While it is possible for the water extracts of cinnamon and *Radix Astragali* to be administered alone without other excipients, it is preferable to formulate the active ingredient as a pharmaceutical or neutraceutical formulation. For example, the formulation may include diluents or excipients such as fillers, binders, wetting agents, disintegrators, surface-active agents, lubricants and the like. Typical unit dosage forms include tablets, pills, powders, solutions, suspensions, emulsions, granules, capsules, suppositories. Each carrier is compatible with other ingredients in the formulation and is biologically acceptable to the subject and inert.

Formulations include those suitable for oral and parenteral (including subcutaneous, intramuscular, intravenous and intradermal) administration, with oral formulations being preferred. A preferred oral formulation is an encapsulated dry powder of a water extract of cinnamon, a water extract of *Radix Astragali*, or a mixture of both water extracts.

Chromium, generally in the form of chromium picolinate or chromium chloride, can optionally be added in the formulation comprising a water extract of cinnamon, a water extract of *Radix Astragali*, or a mixture of both water extracts, to provide a beneficial effect. Alternatively, chromium, generally in the form of chromium picolinate or chromium chloride, can be administered separately.

Zinc, for example, in the form of oral zinc sulfate, zinc supplements, or zinc+MVM (multivitamin/mineral), can optionally be added in the formulation comprising a water extract of cinnamon, a water extract of *Radix Astragali*, or a mixture of both water extracts, to provide a beneficial effect. Alternatively, zinc can be administered separately.

The formulations can be conveniently prepared in unit dosage form and can be prepared by any method known in the art.

For example, to prepare formulations suitable for injection, solutions and suspensions are sterilized and are preferably isotonic to blood. In making injectable preparations, carriers which are commonly used in this field are used, for example, water, ethyl alcohol, propylene glycol, ethoxylated isostearyl alcohol, polyoxylated isostearyl alcohol, polyoxyethylene sorbitol and sorbitate esters. In these instances, adequate amounts of isotonicity adjusters such s sodium chloride, glucose or glycerin can be added to make the preparations isotonic. The aqueous sterile injection solutions may further comprise oxidants, buffers, bacteriostats, and like additions acceptable for parenteral formulations.

The formulation according to the invention can be administered by any suitable routes, including oral and parenteral (including intraperitoneal, subcutaneous, intramuscular, intravenous and intradermal) routes. It will be appreciated that the preferred route will vary with the condition and age of the patient, and how long-lasting the treatment is.

The present invention provides a method for increasing glucose uptake or regulating blood glucose levels in a subject, by administering to a subject an effective amount of a water extract of Cinnamon and an effective amount of a water extract of *Radix Astragali*.

The present invention provides a method for lowering blood glucose levels in a hyperglycemic subject, by administering to a hyperglycemic subject an effective amount of a water extract of Cinnamon and an effective amount of a water extract of *Radix Astragali*.

The present invention also provides a method for preventing a subject from developing type 2 diabetes, by administering to a normal or pre-diabetic subject an effective amount of a water extract of Cinnamon and an effective amount of a water extract of *Radix Astragali*.

The present invention also provides a method for lowering total cholesterol, LDL-cholesterol and triglyceride levels in a subject, by administering to a subject an effective amount of a water extract of Cinnamon and an effective amount of a water extract of *Radix Astragali*.

The effective amount will vary depending upon several factors, including, but not limited to, the age and weight of the patient, the type of the disease state treated, how advanced the disease state is, the general health of the patient, the severity of the symptoms, whether the water extract of cinnamon and the water extract of *Radix Astragali* are administered alone or in combination with other active ingredients, the incidence of side effects, and the like. Generally, a human subject may take 1-10 capsules containing the water extract of cinnamon and the water extract of *Radix Astragali* for treatment. Each capsule contains 100-1000 mg of dry powder of a water extract of cinnamon alone, a water extract of *Radix Astragali* alone, or a mixture thereof. Preferred daily use in a human subject is 500-5000 mg total of water extracts of cinnamon and *Radix Astragali*. When a composition such as a capsule contains a mixture of a water extract of cinnamon and a water extract of *Radix Astragali*, the weight ratio of cinnamon extract to *Radix*

*Astragali* extract is in general from about 3:1 to 1:5, with about 1:1 to 1:2 or about 1:1 to 1:3 being preferred. About equal weight ratio (1:1±10%) of cinnamon to *Radix Astragali* is more preferred. Chromium, in an amount of about 100-300 μg, usually about 200 μg, can be added into the composition. Zinc, in an amount of 5-100 mg or 15-50 mg/day, can be added into the composition.

The amount of total active ingredients, i.e., the dry powder of both cinnamon water extract and *Radix Astragali*, free of solid debris, ranges from 25-10,000 mg, preferably 100-1000 mg, 200-1000 mg, 200-2500 mg, 500-1500 mg, or 500-2500 mg, to be administered to a human subject per day. The dry powder additionally can include chromium, in an amount of 100-3000 μg or 100-300 μg, to be administered to a subject per day. The dry powder further can include zinc, in an amount of 10-100 mg or 15-50 mg to be administered to a subject per day.

The following examples are presented as illustrations, not limitations.

EXAMPLES

Example 1. Glucose Uptake of Water Extract of Test Compounds

Objectives

The purpose of this experiment is to find a plant that can provide a synergistic insulin-like activity when combining with cinnamon.

Plants

Roots of *Rhizoma Coptdis* (A), roots of *Radix Astragali* (B), roots of Chinese Foxglove (C), dried melon of *Momordica Charantiap* (D) were purchased from Beijing Chinese Medicine Pharmacy. Dried leaves of *Begonia Fimbristipulata Hance* (E) was purchased from Zhaoqing Food Store, Guangdong, China. A and E are herbs used in Chinese medicine.

10 g of A and D was each passed through a 30 mesh screen and suspended in 100 ml water. B, C, and E were not applied to the 30 mesh screen because B was fibrous, C was sticky, and E was already fine. Then A-E each in 100 ml water was incubated at 80° C. for 2 hr. They were then centrifuged at 5000 rpm for 20 min and 50 ml of each supernatant was collected and freeze-dried. The yield of each compound was: A—26%, B—19%, C—74%, D—46%, E—26%. Water extract of cinnamon was prepared according to U.S. Pat. No. 6,200,569. Dry powder of water extract of A-E and cinnamon was each dissolved in water to a concentration of 100 mg/ml.

Glucose Uptake.

2-NBDG (2-(N-(7-Nitrobenz-2-oxa-1,3-diazol-4-yl) Amino)-2-Deoxyglucose) uptake was measured as previously described (Zou et al. *J. Biochem. Biophys. Methods,* 2005, 64, 207-215; Nitin et al., *International journal of cancer. Journal international du cancer,* 2009, 124, 2634-42) with some modifications.

The mouse embryonic fibroblast cell line 3T3-L1 is a model for metabolism and obesity research, because the cells can be chemically induced to differentiate into adipocytes. 3T3-L1 (ATCC® CL-173™) cells ($1\times10^4$ cells/well) were plated in a 96-well microplate and incubated in Dulbecco's modified Eagle's medium (DMEM, ATCC® 30-2002™) supplemented with pen/strep (100 U/ml of penicillin and 100 U/ml of streptomycin) and 10% calf serum in an atmosphere of 5% $CO_2$ at 37° C. After 24-hr, cells were cultured in 200 μL of low-glucose supplemented culture media only as a control (Invitrogen, #11885-092) for 3 hours. The cells were also cultured in 200 μL of the same culture media added with 100 μg/mL of water extracts of different test compounds (cinnamon, A, B, C, D, E, cinnamon+A, cinnamon+B, cinnamon+C, cinnamon+D, cinnamon+E), or 1 μM/10 μM of insulin for 3 hours. The media was then changed with glucose-free culture media containing 50 μM 2-NBDG (Invitrogen, #N13195). After 30 min, cells were washed using a pre-warmed phosphate-buffered saline (PBS) solution. Cells were imaged live using a fluorescence microscope (Zeiss LSM 510 (Carl-Zeiss Inc., Thornwood, N.Y.)) using 488-nm laser excitation and a BP 530-580 nm emission filter. Images were quantified as mean fluorescence intensity using an ImageJ program (Version 1.48v).

Results

The average ratios (n=2) of fluorescence intensity in cells of test compounds or insulin to control (normalized to 1) are calculated. FIG. 1 show the calculated ratios; the SEM values are shown in error bars. After the fluorescence intensity of control is subtracted, the calculated results show that cinnamon (Cin) plus *Radix Astragali* (B) provides a synergistic activity in comparison with cinnamon alone and *Radix Astragali* alone. The results indicate that cinnamon (Cin) plus *Radix Astragali* (B) enhanced the activity of cinnamon alone and provides improved insulin sensitivity and/or enhanced an insulin-like action. The results also show that adding *Rhizoma Coptdis* (A), Chinese Foxglove (C), *Momordica Charantiap* (D), or *Begonia Fimbristipulata Hance* (E) to cinnamon did not enhance the activity of cinnamon.

Example 2. Pilot Clinical Study

People of 35-65 years of age, free of disease other than Type II diabetes, with a fasting blood glucose of 7.2-15.5 mmol/L, 2-hour blood glucose of 9.4-16.7 mmol/L and a hemoglobin$A_{1c}$, of 8.0-12%, are selected for pilot study. Patients continue their regular treatment for diabetes, for example, sulfonylurea drugs, insulin, or no medication.

Each of seven groups of patients each take different capsules. There are 3-5 patients in each group and they are each treated for 1-3 months with 2 capsules per day each containing 500, 1000, or 2000 mg dry extract powder per day administered orally. The capsules taken by each group contain dried powder of water extract of cinnamon and water extract of *Radix Astragali* in 1:1 weight ratio. A control group will take placebo capsules.

Blood glucose, hemoglobin$A_{1c}$, insulin, total cholesterol, LDL cholesterol, HDL cholesterol and triglycerides are measured in each patient at time zero, one, two and three months.

Example 3. Case Studies

Patient A is a 67 year old female with 11 years of type 2 diabetes history.

Patient B is a 79 year old female with 16 years of type 2 diabetes history.

Patient C is a 76 year old female with 3 years of type 2 diabetes history.

Each patient took one capsule (containing 250 mg of water extract of Cinnamon bark and 250 mg of water extract *Radix Astragali*) twice a day for 4 months. Different parameters such as triglycerides (TG), HLD, LDL, blood pressure (BP) were tested for each patient, and the results are summarized below in Table 1.

TABLE 1

| Patient | TG Baseline mmol/L | TG Treated mmol/L | HDL Baseline mmol/L | HDL Treated mmol/L | LDL Baseline mmol/L | LDL Treated mmol/L | BP Systolic/ disastolic Baseline mmHg | BP Systolic/ disastolic Treated mmHg |
|---|---|---|---|---|---|---|---|---|
| A | 2.42 | | 1.33 | | | | | |
| A | | 1.94 | | 1.49 | | | | |
| B | | | 1.43 | | 4.13 | | | |
| B | | | | 1.70 | | 3.64 | | |
| C | | | | | | | 140/90 | 127/74 |

The results showed that after treatment, patient A decreased her triglycerides from high to borderline high (2.42 to 1.94 mmol/L) and increased her HDL from 1.33 to 1.49 mmol/L; patient B decreased her LDL from high to borderline high (4.13 to 3.64 mmol/L) and increased her HDL from 1.43 to 1.70 mmol/L; and patient C decreased his Systolic blood pressure (140 to 90 mmHg) and diastolic blood pressure (127 to 74 mmHg), which indicate a change from stage 1 hypertension to pre-hypertension or normal stage.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude this specification.

What is claimed:

1. A method for lowering serum low density lipoprotein (LDL)-cholesterol and/or triglycerides in the blood of a subject in need thereof, comprising administering to the subject an effective amount of a composition consisting essentially of a water extract of *Cinnamomum* bark and a water extract of *Radix Astragali*, wherein the water extracts are administered in a total amount of 200-2500 mg/day, and wherein the weight ratio of the water extract of *Cinnamomum* bark and the water extract of *Radix Astragali* is about 1:1.

2. The method according to claim 1, wherein the method does not include a step of administering another active ingredient that increases insulin sensitivity or provides insulin-like action.

3. The method according to claim 1, wherein said method lowers LDL-cholesterol.

4. The method according to claim 1, wherein said method lowers triglycerides.

5. A method for increasing serum high density lipoprotein (HDL)-cholesterol in the blood of a subject in need thereof, comprising administering to the subject an effective amount of a composition consisting essentially of a water extract of *Cinnamomum* bark and a water extract of *Radix Astragali*, wherein the water extracts are administered in a total amount of 200-2500 mg/day, and wherein the weight ratio of the water extract of *Cinnamomum* bark and the water extract of *Radix Astragali* is about 1:1.

6. The method according to claim 5, wherein the method does not include a step of administering another active ingredient that increases insulin sensitivity or provides insulin-like action.

7. A method for lowering blood pressure in a hypertensive subject, comprising administering to the subject an effective amount of a composition consisting essentially of a water extract of *Cinnamomum* bark and a water extract of *Radix Astragali*, wherein the water extracts are administered in a total amount of 200-2500 mg/day, wherein the weight ratio of the water extract of *Cinnamomum* bark and the water extract of *Radix Astragali* is about 1:1.

8. The method according to claim 7, wherein the method does not include a step of administering another active ingredient that increases insulin sensitivity or provides insulin-like action.

* * * * *